United States Patent [19]

Yamaka et al.

[11] Patent Number: 4,483,326
[45] Date of Patent: Nov. 20, 1984

[54] CURVATURE CONTROL MECHANISM IN ENDOSCOPES

[75] Inventors: Shiyouichi Yamaka, Kamifukuoka; Hirohisa Ueda, Tokyo, both of Japan

[73] Assignee: Kabushiki Kaisha Medos Kenkyusho, Japan

[21] Appl. No.: 370,274

[22] Filed: Apr. 20, 1982

[30] Foreign Application Priority Data

Apr. 21, 1981 [JP] Japan .............................. 56-58211[U]
Jul. 4, 1981 [JP] Japan .............................. 56-99677[U]

[51] Int. Cl.³ .............................................. A61B 1/06
[52] U.S. Cl. ...................................................... 128/4
[58] Field of Search ........................ 128/4, 5, 6, 7, 8, 9

[56] References Cited

U.S. PATENT DOCUMENTS

| | | | |
|---|---|---|---|
| 2,975,785 | 3/1961 | Sheldon | 128/6 |
| 3,071,161 | 1/1963 | Ulrich | 128/4 |
| 3,253,524 | 5/1966 | Ashizawa et al. | 128/4 |
| 3,610,231 | 10/1971 | Takahashi | 128/6 |
| 3,788,303 | 1/1974 | Hall | 128/4 |
| 3,892,228 | 7/1975 | Mitsui | 128/4 |
| 4,108,211 | 8/1978 | Tanaka | 128/4 |
| 4,236,509 | 12/1980 | Takahashi et al. | 128/4 |
| 4,294,233 | 10/1981 | Takahashi | 128/4 |

FOREIGN PATENT DOCUMENTS 2441222 3/1975 Fed. Rep. of Germany .......... 128/4

Primary Examiner—Edward M. Coven
Assistant Examiner—Max F. Hindenburg
Attorney, Agent, or Firm—Steinberg & Raskin

[57] ABSTRACT

A curvature control mechanism in an endoscope is disclosed. The endoscope is of the type which has a manipulator unit to which a flexible tubular member is connected and whose front end region constitutes a bendable portion. A knob member is rotatably mounted on the manipulator unit and control wires extend from the manipulator unit through the flexible member to the bendable portion so the latter can be bent by the wires in a selectively controlled manner through rotation of the knob. The curvature control mechanism includes a double cylinder type drum device including two drums fixedly mounted on a rotary shaft coupled to the knob. A pair of elongate resilient strips are wound around respective drums in mutually opposite directions and one end of each of the resilient strips is coupled to a respective control wire such that rotation of the drums in one direction causes a take-up of one of the elongate strips on its respective drum and a tension-relief in the other of the resilient strips in the form of a diametric expansion thereof, such expansion preventing an excessive slackness in the control wire to which that resilient strip is coupled while maintaining at least some tension in that control wire.

10 Claims, 9 Drawing Figures

CURVATURE CONTROL MECHANISM IN ENDOSCOPES

BACKGROUND OF THE INVENTION

The present invention relates generally to endoscopes and, more particularly, to mechanisms in endoscopes for controlling the curvature of a bendable portion defined by the front end region of the flexible tubular member of the endoscope.

In endoscopes of the type which are adapted to be inserted into a body cavity for purposes such as the diagnosis, treatment, and/or operation of a digestive organ or the like, the bendable portion constituting the free front end region of the flexible tubular member which has been inserted into the body cavity must be bent in a controlled manner through external manipulation of components of the endoscope. To this end, various mechanisms for controlling the curvature of the bendable portion of the endoscope have been proposed. Many of the curvature control mechanisms utilize an arrangement wherein a plurality of control wires extend parallel to one another from the forward bendable portion through the flexible tubular member or intermediate portion of the endoscope to a manipulator unit to which the flexible tubular member is attached. The application of a pulling or tension force on one of the control wires results in a tension-relief of another control wire so that a desired curvature of the bendable portion of the endoscope is achieved.

Various improvements in curvature control mechanisms used in connection with the arrangement described above have been suggested. Many of these suggested improvements are directed to solving the problem of the presence of excessive slackness in the control wire which is tension-relieved. In other words, improvements have been suggested whereby the control wire which is moved in the direction away from the tension-loaded side will be provided with a required degree of slackness with any excessive slackness being effectively eliminated so that the tension-relieved wire will not become entangled or irregularly stagnated so that a desired curvature control is reliably achieved in a relatively smooth manner.

In an arrangement wherein curvature control is achieved by pulling one of a plurality of wires while another wire is tension-relieved, guide holes are generally provided through which the control wires extend both in the flexible tubular member as well as in the bendable front end portion thereof. These guide holes have diameters which are slightly larger than the outer diameter of each control wire passing therethrough in order to assure a desired smoothness in the manipulation of the curvature control mechanism. In consequence, as understood by those skilled in the art, when the bendable front end portion is bent, the control wire on the tension-loaded side is slidably moved or drawn through a series of guide holes along the sections of their inner walls which are remote from the longitudinal axis of the bendable front end portion. On the other hand, the control wire on the tension-relieved side is slidably moved through its series of guide holes along sections of their inner walls which are nearer to the longitudinal axis of the bendable portion. As a result, the length of the control wire on the tension-relieved side which is actually delivered forwards during the bending operation is shorter than the length of the wire on the tension-loaded side which is actually taken up, and this necessitates an excessive slack. Moreover, the control wire on the tension-loaded side will often stretch or extend along itself and, in such case, the wire will be pulled with an excess of this extension or stretched amount to obtain the desired curvature. Consequently, the length of the control wire on the tension-relieved side to be delivered forwards during the bending operation will be yet even shorter than the length to be pulled and the wire on the tension-relieved side will have an even further excessive slackness which may result in the wire being flexed, bent or forcibly compressed within the guide holes causing entanglement, stagnation or untwisting. This in turn may cause a serious obstacle to the smooth manipulation of the mechanism. Such circumstances which occasionally occur in prior art apparatus have sometimes caused fatal accidents, such as when a control wire breaks since such an accidental breakage of a control wire in an endoscope which had already been inserted into the body cavity with the forward bendable portion thereof already in a curved condition will render it difficult to remove the endoscope from the body cavity. It is clear that such a circumstance is extremely dangerous in the use of endoscopes in diagnosis, treatment or operation. Thus, it is already known that the slackness inevitably generated in the control wire on the tension-relieved side, which slackness is not only unnecessary but also detrimental in the operation of the endoscope, must be absorbed or eliminated in order to overcome the problems discussed above and to this end various suggestions have been proposed. However, conventional prior art mechanisms incorporating such suggestions have not entirely solved the problem since such suggestions involve not only merits but also are encumbered with certain disadvantages.

For example, an arrangement is disclosed in Japanese Utility Model Disclosure Gazette No. 1974-80087 where each control wire is provided with a coil spring along a portion of the associated channel through which the wire is guided so that the wire on the tension-loaded side will be subjected to a tension by such a coil while an excessive slackness in the wire on the tension-relieved side will be absorbed by a self-compression of the associated coil spring. However, in this arrangement, a control wire must be continuously biased under tension of the coil spring to absorb the slackness due to excessive tension-relief and it has been found difficult to maintain the biasing characteristic of the coil spring in view of the fact that the spring unavoidably becomes fatigued in operation. When a coil spring having a greater biasing effect is utilized in an attempt to compensate for this problem, the heavier loads thereby presented prevents a smooth manipulation of the mechanism. On the other hand, when a coil spring having a lower biasing effect is utilized, the wire on the tension-loaded side cannot be adequately pulled or drawn while the excessive slackness in the wire on the tension-relieved side cannot be satisfactorily absorbed or eliminated.

In another proposed arrangement disclosed in Japanese Patent Disclosure Gazettes Nos. 1977-144177 and 1977-144178, a separate elastic member is provided which is adapted to maintain the control wire on the tension-relieved side in a tensioned condition.

Many other suggestions have been made in addition to those discussed above. Thus, Japanese Patent Disclosure Gazette No. 1978-105079, Japanese Utility Model Disclosure Gazettes Nos. 1978-116180 and 1977-158586, and Japanese Utility Model Publication No. 1976-43030 disclose an arrangement wherein the free end of each control wire is provided with a projection and a corresponding member provided which is adapted to be engaged by the projection so that the wire is tension-loaded by such engagement when the wire is pulled on the tension-loaded side while, on the tension-relieved side, a slackness is eliminated as the member is freely disengaged from the corresponding projection.

In another proposed arrangement, the control wire is pulled through the rotation of a rotary pulley which is formed in a manner such that its effective radius varies as the pulley is rotated (see Japanese Utility Model Disclosure Gazette No. 1975-49283).

Still further, an arrangement is disclosed in Japanese Utility Model Disclosure Gazette No. 1979-108590 wherein a take-up pulley and a rewinding pulley are rotated by a common manipulating knob. Predetermined play or tolerances are provided in opposite directions between a rotation transmitting shaft so that the two pulleys are rotated by that rotation transmitting shaft in a manner such that, on the rewinding side, the rewinding pulley will have an idle rotation as a spring on the rewinding side is compressed.

None of the prior art arrangements which have been suggested heretofore have proven to be entirely satisfactory. Thus, the prior art suggestions have disadvantages and difficulties such as being relatively mechanically complicated and requiring relatively bulky dimensions resulting from the necessity of incorporating a plurality of separate components into the mechanism.

SUMMARY OF THE INVENTION

Accordingly, one object of the present invention is to provide a new and improved curvature control mechanism in an endoscope which eliminates the drawbacks discussed above.

Another object of the present invention is to provide a new and improved curvature control mechanism in an endoscope having the capability of eliminating the slackness present due to excessive tension-relief and which is not encumbered by drawbacks inherent in prior art techniques.

Still another object of the present invention is to provide a new and improved curvature control mechanism in an endoscope which is capable of curvature control and the elimination of slackness by light manipulation and without substantial variation in use over many years.

Briefly, in accordance with one embodiment of the present invention, these and other objects are attained by providing a curvature control mechanism wherein in order to avoid an effective increase in the winding diameter of the take-up drum as the manipulating knob is rotated, the control wires themselves are not wound directly around the associated drums but rather, elongate resilient strips in the form of leaf spring members which are connected to respective control wires are wound around the associated drums in a manner such that when one of the take-up drums is rotated in the take-up direction, the other take-up drum is rotated in an unwinding direction and the elongate leaf spring member which has been tightened around this other drum is progressively slackened and expanded within a narrow space defined around the unwinding drum so as to achieve a satisfactory elimination of slackness. In this manner, it is possible to provide even a multiple-winding of the elongate resilient leaf spring members around the take-up drums so that the spring members take the form of spiral springs so that consequently a sufficient allowance for the slackness of the elongate resilient spring members due to rewinding is provided as in a watch barrel to achieve a desired degree of absorbtion or elimination of slackness.

In accordance with another embodiment of the invention, the elongate resilient strips take the form of lengths of resilient wire, such as piano wire, cable or the like. The take-up drums are constituted as a pair of pulleys fixedly mounted on the rotary shaft of the knob, each pulley having a thin, relatively deep groove formed around its circumference in which a respective one of the resilient wire is multiply wound in a flat spiral configuration. The width of the groove of each pulley is slightly greater than the diameter of the resilient wire and the depth of the groove is sufficient to allow a flat spiral multiple-winding of the resilient wire around the pulley and, moreover, to allow for an expansion of the spiral windings of the resilient wire therewithin. When one of the pulleys is rotated in the take-up direction, the other pulley is rotated in an unwinding direction and the resilient wire which is tightly wound within the thin, deep groove of that pulley is progressively slackened and expanded within the groove while remaining therein so as to achieve a satisfactory elimination of slackness of the control wire to which it is connected.

A multiple-winding of the elongate resilient strips around the associated drums or within the grooves of the pulleys assures the provision of the necessary adequate strength for the mechanism and will reliably avoid all undesirable phenomena, such as entanglement of the control wire in itself or displacement of the control wire from its proper path of winding which might occur when the control wire itself is multiple-wound around the pulley.

Finally, the elongate resilient strips are respectively wound around the substantially identical but separate take-up drums or pulleys in mutually opposite directions in accordance with the present invention so that the control wire on the pulled or tensioned side is always maintained under a necessary tension thereby permitting the rewinding stroke to be minimized, on the one hand, while permitting the bendable front end portion to be curvature-controlled over a relatively wide range on the other hand. Thus, a desired operation of the curvature control mechanism can be accomplished with an advantageously compact structure.

DESCRIPTION OF THE DRAWINGS

The present invention and many of the attendant advantages thereof will be readily appreciated as the same becomes better understood by reference to the following detailed description when considered in connection with the accompanying drawings in which.

DESCRIPTION OF THE PREFERRED EMBODIMENTS

Figure 1:
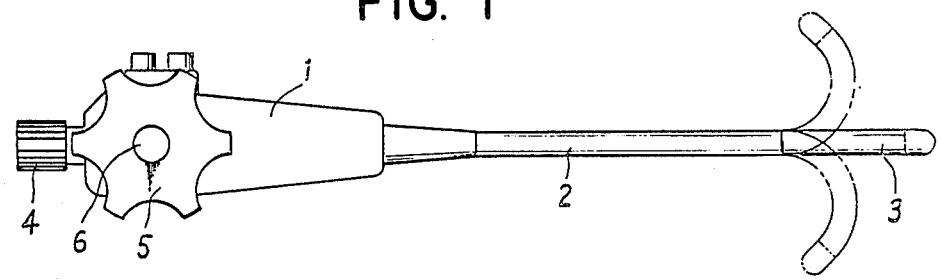
FIG. 1 is a plan view of an endoscope provided with a curvature control mechanism constructed in accordance with the present invention.
Figure 3:
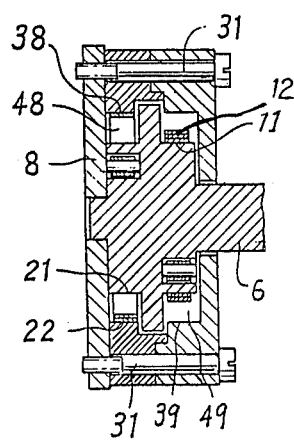
FIG. 3 is a section view taken along line 3—3 in FIG. 2.
Figure 4:
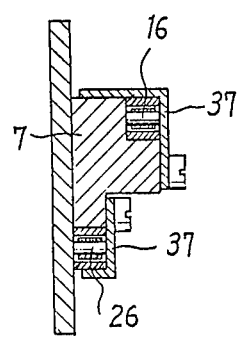
FIG. 4 is a sectional view taken along line 4—4 in FIG. 2.
Figure 5:
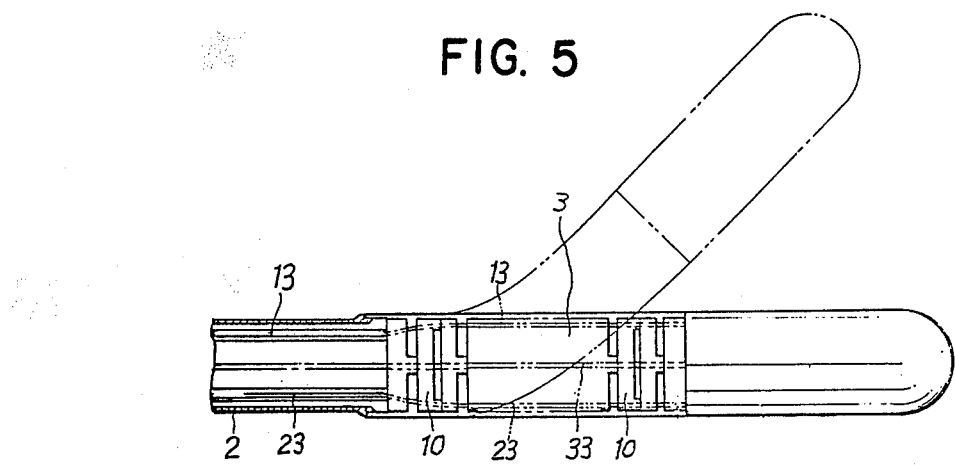
FIG. 5 is a plan view, partially broken away, of a bendable portion constituting the front end of an endoscope equipped with a curvature control mechanism in accordance with the present invention.
Figure 6:
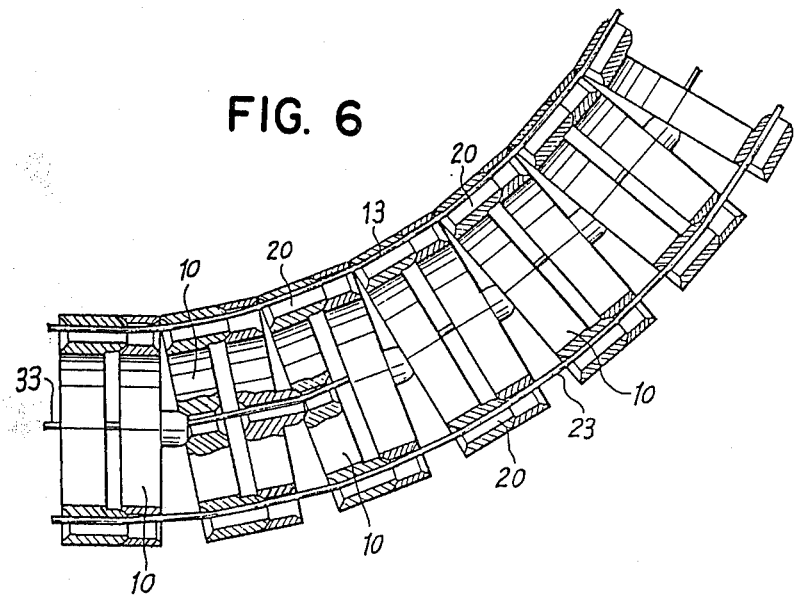
FIG. 6 is a plan view in section illustrating, on an enlarged scale, part of the bendable portion of an endoscope after bending.

Referring now to the drawings wherein like reference characters designate identical or corresponding parts throughout the several views, and more particularly to the embodiment of the invention illustrated in FIGS. 1-4 and in conjunction with FIGS. 5 and 6, an endoscope equipped with a curvature control mechanism in accordance with the present invention is illustrated in FIG. 1. The endoscope has a manipulator unit 1, a flexible tubular portion 2 connected thereto and a bendable portion 3 at the forward end region of the flexible tubular portion 2. As in conventional endoscopes, the front end of the bendable portion 3 is provided with an optical element for providing visual access therefrom and an ocular optical system for observation is incorporated at the rear end 4 of the endoscope.

The bendable portion 3 is adapted to be controllably curved or bent as shown by the double-dotted chain lines in FIGS. 1 and 5 through suitable rotation of a knob 5 on the manipulator unit 1. It is understood that although the bendable portion 3 is illustrated in the figures as being bent in a lateral direction within a single plane, it is also possible for the bendable portion to be curved or bent by another knob in a plane extending transversely to the first-mentioned plane. Since such an arrangement would be substantially identical in construction to the arrangement illustrated herein and described below, a depiction of such an arrangement has been omitted.

Referring to FIGS. 2-6, according to the invention, double cylinder type drum means is rotatably mounted in the manipulator unit 1, the drum means comprising two drums 11 and 21. In the illustrated embodiment, the drum means comprises an integral unit on which the cylindrical drums 11 and 21, preferably having substantially identical diameters, are formed with a peripherally extending flange separating the drums from each other. Moreover, the drum means are formed integrally with a rotatably mounted shaft 6 for rotation therewith, the rotary shaft 6 being mounted in a manipulator unit 1 and adapted to be rotated by rotation of the knob 5. It is understood that the double cylinder type drum means may be otherwise formed, e.g. with the drums being separately formed.

According to a feature of the present invention, a pair of elongate resilient strips are wound around the respective drums in mutually opposite directions. Thus, in the illustrated embodiment, a pair of thin leaf springs 12 and 22 have one of their respective ends secured by respective anchoring means 14 and 24 to their associated drums 11 and 21, respectively. The other ends of the thin leaf springs 12 and 22 are connected in a manner described below to respective control wires 13 and 23 which are adapted to be tensioned and slackened through manipulation of the curvature control mechanism.

The control wires 13 and 23 extend respectively through guide members 19 and 29 (FIG. 2) through the flexible tubular portion 2, and then through respective guide openings 20 (FIG. 6) formed in opposed outer sides of flexibly articulated elements 10 which together constitute the bendable portion 3. The forward ends of the control wires extend to the front end portion or front end element of the bendable portion to which they are fastened. Guide seats 7 are mounted within the manipulator unit 1 for slidably guiding clamping connectors 15 and 25 which couple associated ends of the leaf springs 12 and 22 to the ends of control wires 13 and 23. As shown, the clamping connectors 15 and 25 are in the form of cylindrical containers in which slits are formed in the inner end walls thereof and respective rolled portions 16 and 26 of the leaf springs 12 and 22 are inserted into the containers through the slits so as to be supported by the inner end walls of the containers. The ends of the control wires 13 and 23 are passed through the bores of respective adjusting cylinders 18 and 28 and caps 17 and 27 or the like enlarge the ends of the control wires to prevent their withdrawal from the adjusting cylinders. Moreover, the adjusting cylinders 18 and 28 through which the respective control wires 13 and 23 extend are threaded into the respective clamping connectors 15 and 25, i.e., threads formed in the outer cylindrical surfaces of the respective adjusting cylinders are engaged with threads correspondingly formed in the inner cylindrical walls of the respective clamping connectors 15 and 25 so that the control wire 13 and the leaf spring 12, on the one hand, and the control wire 23 and the leaf spring 22, on the other hand, may be connected to each other under a desired tension. In other words, the adjusting cylinders 18 and 28 may be adjustably threaded into their respective clamping connectors 15 and 25 so that the control wires 13 and 23 are pulled into the clamping connectors 15 and 25 to obtain the respective desired degrees of tension. In this manner, the clamping connectors 15 and 25 provide for a fine adjustment of the tension under which the respective control wires 13 and 23 are connected to the associated leaf springs 12 and 22.

Bearing brackets 8 (FIG. 3) support the rotatable shaft 6 and a bearing 9 is provided comprising the bearing brackets 8 and screws 31. According to the invention, annular spaces 48 and 49 are defined between the inner peripheral surfaces 38 and 39 of the respective bearing brackets 8 and the drums 11 and 21 which are in respective opposed relationship thereto. Thus, in accordance with the illustrated embodiment, means are provided for defining respective annular spaces around the drums and it is understood that the particular structure for defining these annular spaces with respect to the cylindrical outer surfaces of the respective drums may be different from that illustrated. It is also seen that the diametric width of the respective annular spaces 48 and 49 are substantially the same.

Figure 2:
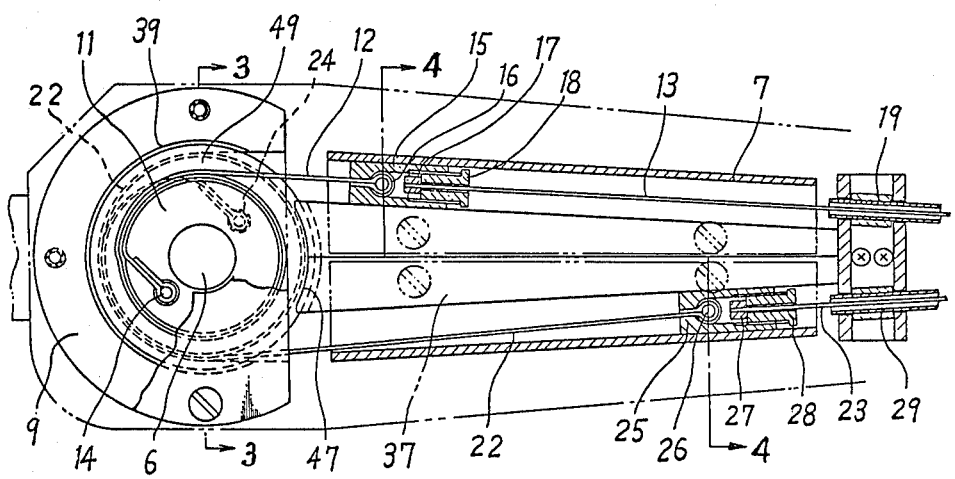
FIG. 2 is a view, partially broken away and sectioned, of a curvature control mechanism in accordance with the present invention with the manipulator unit of the endoscope in which the mechanism is situated being shown in phantom.

Covers 37 are provided for covering the respective guide seats 7. As seen in FIG. 2, each of the covers 37 is formed having a region formed in the shape of a circular arc 47 which is in opposed relationship to the drums 11 and 12 so as to extend the annular spaces 48 and 49 further around the circumference of the drums, i.e., so as to prevent the associated leaf springs from becoming slackened in an irregular manner as will become clearer hereinbelow.

Referring to FIG. 6, another control wire 33 is illustrated which functions to bend the bendable portion 3 in a direction substantially perpendicular to that in which the bendable portion 3 is curved or bent by the wires 13 and 23. As already mentioned hereinabove the control wire 33 is operated by a separate knob (not shown).

In operation, with the curvature control mechanism constructed in accordance with the embodiment described above, the knob 5 may be manually rotated, e.g., counter-clockwise, as seen in FIG. 2, whereupon the leaf spring 12 anchored on the drum 11 by anchoring means 14 is taken-up on the drum 11 in order to pull the control wire 13 via clamping connector 15 to bend the bendable portion 3 as shown in FIGS. 5 and 6. At the same time, the other leaf spring 22 wound around the drum 21 and anchored thereto by anchoring means 24 is slackened in the form of a spiral spring within the associated annular space 48 as shown in FIG. 3 and by the broken lines in FIG. 2. Meanwhile, the other end of leaf spring 22 functions to feed the control wire 23 in a forward direction by a desired length. It is important to note, however, that in actuality, a length somewhat greater than desired will tend to be slackened. However, such excessive slackness will be effectively absorbed since the leaf spring 22 is rewound and expanded within the annular space 48 defined between the drum 21 and the inner peripheral surface 38 of the associated bearing bracket which is in opposed relationship to the cylindrical surface of drum 21. In other words, the leaf spring 22 rewound around its associated drum is pulled as the control wire 23 itself is pulled by a length determined by the desired degree of curvature or bending of the bendable portion 3. However, a slackness in excess of the desired length will be absorbed through expansion of the leaf spring within the annular space 48 so that the control wire 23 is in fact prevented from being forcibly fed in a forward direction under action of the excessive slackness.

Similarly, when the knob 5 is rotated in a clockwise direction so as to curve or bend the bendable portion 3 in the opposite direction, the leaf spring 22, previously rewound and expanded within the annular space 48, is tightened around the drum 21 and then taken-up thereon so that the control wire 23 is pulled by the leaf spring 22 coupled thereto via the clamping connector 25 to bend the bendable portion 3 in such opposite direction. At the same time, the other leaf spring 12 is rewound and slackened around its associated drum 11. This slackened length of the leaf spring 12 takes the form of an expansion of the leaf spring substantially in the diametrical direction with respect to the drum 11 within the annular space 49 so that only a desired length of the control wire 13 is pulled in the direction of the bendable portion 3 under tension of the leaf spring 12.

As in apparent from the foregoing description, the control wires are themselves not directly wound around any drums or pulleys in the curvature control mechanism according to the present invention. Accordingly, the control wire on the tension-relieved side will not only be free from irregular stagnation but, additionally, will be free from the undesirable effect of being forcibly delivered forwards. As a result, the subsequent taking-up procedure is achieved in a smooth manner without any hindrance.

Moreover, it should be noted that during the taking-up operation, the tension-relieved elongate resilient strip is expanded around its associated drum in a manner such that the control wire connected thereto will be maintained under a certain tension, i.e., under a condition wherein the control wire on the tension-relieved side can always be delivered forwards by the precise require length and without the various drawbacks which are often encountered inconventional mechanisms, such as the propogation of a waving or bending force which might easily result in the damage or even in the breakage of the control wires and/or the entanglement or clogging of the control wires in the course of their movement.

Although the present invention has been described hereinabove with respect to an embodiment in which the elongate resilient strips take the form of leaf springs, it is understood that the elongate resilient strips may be formed of other elements such, for example, as piano wire, having a substantially circular cross-section or cable-type twisted wire, so long as the selected elongate strips have the necessary resiliency, elasticity and strength.

Figure 7:
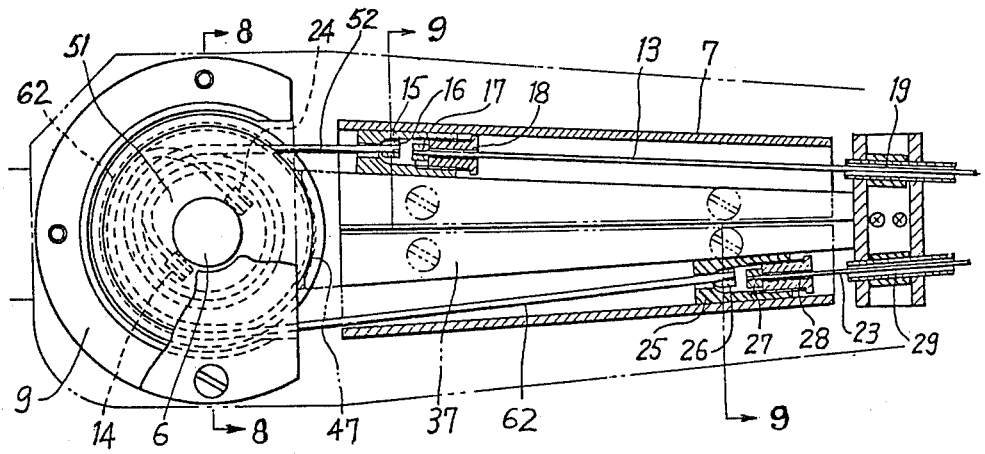
FIG. 7 is a view similar to FIG. 2 illustrating another embodiment of a curvature control mechanism in accordance with the present invention.
Figure 8:
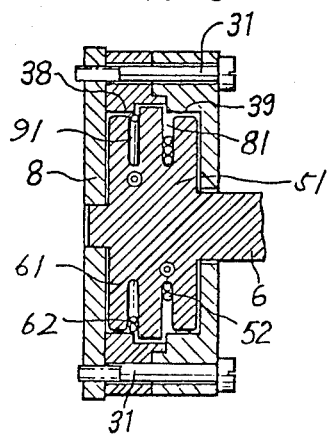
FIG. 8 is a section view taken along line 8—8 in FIG. 7.
Figure 9:
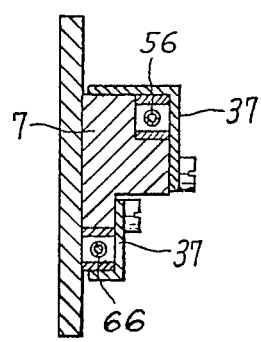
FIG. 9 is a section view taken along line 9—9 in FIG. 7.

In connection with the foregoing, another embodiment of the invention is illustrated in FIGS. 7-9 wherein the elongate resilient strips, rather than comprising leaf springs 12 and 22, are constituted by piano wires 52 and 62 having a substantially circular cross-section. In this embodiment of the invention it has been found advantageous to utilize a double cylinder type drum means in the form of a pair of pulleys in each of which a thin, deep circumferential groove is formed having a width which is slightly greater than the diameter of the piano wire in view of the multiple-winding of the wire around the drum.

Thus, referring to FIGS. 7-9, wherein the same reference numerals are used to designate identical or corresponding parts as those described above in connection with the embodiment illustrated in FIGS. 1-4, piano wires 52 and 62 are wound around pulleys 51 and 61 in which a respective pair of parallel grooves 81 and 91 are provided around the circumference thereof. The piano wires 52 and 62 are wound in the respective grooves 81 and 91 in mutually opposite directions and are anchored at their respective ends to the respective pulleys. When the pulleys are rotated in a counter-clockwise direction, the piano wire 52 will enter into the groove 81 and be spirally wound therein while the other piano wire 62 is slackened in the groove 91 and rewound through the enlargement of its winding diameter. As noted, the width of the grooves 81 and 91 is slightly larger than the diameter of the piano wires 52 and 62 so that a flat spiral winding is achieved as seen in FIG. 8 and the depth of the grooves is determined by the necessary amount of movement of the control wires 13 and 23 required for bending the bendable portion 3 and the winding diameter of drums 51 and 61. It is generally preferable for the grooves 81 and 91 to have a depth which will permit a multiple winding, e.g., 5 to 6 turns or windings of the piano wires 52 and 62 to be situated therein.

Enlarged projections 56 and 66 are provided at the ends of the piano wires 52 and 62 which are inserted into the clamping connectors 15 and 25 so as to retain the ends of the piano wires within the clamping connectors.

According to the illustrated embodiment, the piano wire will be slackened on the pulley which is rewound, e.g., the piano wire 62 will be rewound on the drum 61 as shown in FIGS. 7 and 8. At the same time, the piano wire 62 is slackened within the groove 91 by the windings thereof enlarging their diameters. Thus, the depth of each groove is sufficient to accommodate an expansion of the flat spiral windings of the resilient wire with the wire remaining within the groove. However, it is noted that the slackening will be only in an amount necessary for the control wire 23 to accommodate the bending of the bendable portion 3 and the control wire 23 will be maintained under a tension exerted by the piano wire 62.

The peripheral surfaces 38 and 39 of the bearing brackets are spaced closer to the cylindrical surfaces of the pulleys 51 and 61 and function to prevent the windings of the wires from moving out of the grooves.

In the first embodiment illustrated in FIGS. 2-4 wherein the elongated resilient strips are constituted by leaf springs, the length by which a leaf spring is slackened or expanded within an associated annular space will be sufficient and can be adjusted by providing the leaf spring with an appropriate thickness and an adequate angular distance or number of windings over which the leaf spring is wound around it associated drum.

Accordingly, slackness in a control wire can be satisfactorily absorbed or eliminated even in cases where the endoscope is quite long or where the bendable portion is relatively long so as to enlarge the range of possible curvature. Thus, the use of leaf springs as the elongate resilient strips is extremely effective in broadening the scope to which the endoscopes equipped therewith can be employed. Another advantage resulting from the use of leaf springs as the elongate resilient strips is that the winding diameter will not be substantially increased during operation as in the case where steel wire or cable type twisted wire having a circular cross-section which is thicker than the thickness of a leaf spring is multiply-wound around the drum as in the case of the embodiment illustrated in FIG. 7-9. Accordingly, the space requirements for the control mechanism can be maintained at a desirable minimum. In this connection, even in the case where steel wire or cable-type twisted wire is utilized as the elongate resilient strips, the space required to connect such a wire to the associated control wire need not be overly large since it is no longer necessary to absorb or eliminate the slackness of the control wire in such a space as a result of the present invention. Therefore, the components of the mechanism relating to the manipulation of the control mechanism may advantageously be formed in a more compact manner than in mechanisms of the prior art. Moreover, the diameter of the drums may be maintained relatively small and the knobs used in controlling the curvature need only be lightly rotated using a small force when the relatively thin leaf spring is wound around each associated drum. Any loss in strength due to the use of thinner leaf springs can be compensated by widening the leaf springs in a corresponding manner which also enables the maintenance of the orientation of the leaf spring wound around its respective drum in a constant manner even in cases where the leaf spring is wound in multiple windings around the drum so that a stabilized operation of curvature control is assured without the possibility of entanglement and/or flexure of the control wires.

Regardless as to whether elongate resilient strips are constituted by leaf springs, wire members or other structure, the present invention provides that the control wires themselves are not directly wound around the associated drums but are separately connected at one of their respective ends with an associated elongate resilient strip which is wound around a respective drum. Accordingly, it is the resiliency of the elongate resilient strips themselves and the taking-up operation of these elongate resilient strips onto their respective drums or pulleys, in accordance with the present invention, which advantageously facilitates an adjustment of the tension under which the respective elongate resilient strips are connected to their associated wires to maintain the respective wires under a proper tension.

Regarding the production of the curvature control mechanism of the present invention, the features of the invention advantageously permit the respective members constituting the control mechanism to be manufactured on separate lines and then assembled into separate blocks and finally incorporated into the manipulator unit. This assembly, readjustment and repair can also be easily performed according to the present invention.

Obviously, numerous modifications and variations of the present invention are possible in the light of the above teachings. It is therefore to be understood that within the scope of the claims appended hereto, the invention may be practiced otherwise than as specifically disclosed herein.

What is claimed is:

1. A curvature control mechanism in an endoscope having a manipulator unit, a flexible elongate tubular portion connected at one of its ends to the manipulator unit, a bendable portion at a forward end region of said flexible tubular portion, a knob member rotatably mounted on the manipulator unit, and control wires extending from the manipulator unit through the flexible tubular portion to the bendable portion so that the latter can be bent by the control wires in a selectively controlled manner through rotation of the knob member, said curvature control mechanism comprising:
  a rotary shaft mounted in the manipulator unit adapted to be rotated by rotation of the knob member;
  double cylinder type drum means including two drums fixedly mounted on the rotary shaft for rotation therewith;
  a pair of elongate resilient strips, each resilient strip being wound around a respective drum in a flat spiral with a multiple winding, said resilient strips being wound around the respective drums in said multiple-winding flat spirals in mutually opposite directions; and
  wherein one end of each of said resilient strips is coupled to a respective control wire such that rotation of said drums in one direction to effect bending of the bending portion causes a take-up of one of the elongate resilient strips on its respective drum and a tension-relief in the other resilient strip, said tension-relief being in the form of a diametric expansion of the windings of the flat spiral of said other resilient strip, and wherein any excessive slackness occurring in the wire to which said other resilient strip is coupled and which is to be tension-relieved with respect to a proper length of that wire to be fed forwardly due to the bending of the bending portion is substantially absorbed by the diametric expansion of the windings of the flat spiral of said other resilient strip to which the wire is coupled with at least some tension being maintained in the wire.

2. The combination of claim 1 wherein said elongate resilient strips comprise leaf springs.

3. The combination of claim 1 wherein said elongate resilient strips comprise piano wire having a substantially circular cross-section.

4. The combination of claim 3 wherein each of the two drums of said double cylinder type drum means comprises a pulley type drum having grooves formed over the circumference thereof.

5. A curvature control mechanism in an endoscope having a manipulator unit, a flexible elongate tubular portion connected at one of its ends to the manipulator unit, a bendable portion at a forward end region of said flexible tubular portion, a knob member rotatably mounted on the manipulator unit, and control wires extending from the manipulator unit through the flexible tubular portion to the bendable portion so that the latter can be bent by the control wires in a selectively controlled manner through the rotation of the knob member, said curvature control mechanism comprising:
- a rotary shaft mounted in the manipulator unit adapted to be rotated by rotation of the knob member;
- double cylinder type drum means including a pair of drums having cylindrical outer surfaces, said drums being mounted coaxially on the rotary shaft for rotation therewith;
- means for defining respective annular spaces at least partially surrounding said drums, said means presenting respective inner surfaces in spaced opposed relationship to at least portions of the cylindrical outer surfaces of said respective drums;
- a pair of elongate resilient strips, each strip being wound around a respective drum in a flat spiral with a multiple winding with one end thereof being anchored thereto and situated within the respective annular space defined around the drum, said elongate resilient strips being would around the respective drums in said multiple-winding flat spirals in mutually opposite directions; and
- wherein the other end of each of said resilient strips is coupled to a respective control wire such that rotation of said drums in one direction to effect bending of the bending portion causes one of said elongate strips to be further wound on its respective drum and the winding of the other one of said resilient strips to be diametrically expanded within the annular space around the other one of said drums, whereby said expansion of the winding of the other one of said resilient strips prevents an excessive slackness in the wire to which said other one of said resilient strips is coupled while maintaining at least some tension in that control wire.

6. The combination of claim 5 wherein said double cylinder type drum means comprises said pair of drums which are integrally formed with each other.

7. The combination of claim 5 wherein said means for defining said respective annular spaces around said drums include bearing brackets defining said inner surfaces and which support said rotary shaft.

8. The combination of claim 5 wherein said resilient strips comprise leaf springs and said expanded resilient strip has the configuration of a spiral spring.

9. A curvature control mechanism in an endoscope having a manipulator unit, a flexible elongate tubular portion connected at one of its ends to the manipulator unit, a bendable portion at a forward end region of said flexible tubular portion, a knob member rotatably mounted on the manipulator unit, and control wires extending from the manipulator unit through the flexible tubular portion to the bendable portion so that the latter can be bent by the control wires in a selectively controlled manner through rotation of the knob member, said curvature control mechanism comprising:
- a rotary shaft mounted in the manipulator unit adapted to be rotated by rotation of the knob member;
- double cylinder type drum means including a pair of pulleys fixedly mounted on the rotary shaft for rotation therewith, each pulley having a thin, deep groove formed therein around the circumference thereof, said pair of grooves being substantially parallel to each other;
- a pair of elongate resilient wires, each resilient wire being wound around a respective pulley in a flat spiral with a multiple winding with one end thereof being anchored to the respective pulley and with the windings thereof being situated in the respective grooves formed therein, said resilient wires being wound within the respective grooves in mutually opposite directions;
- each of said grooves having a width slightly greater than the diameter of the respective resilient wire situated therein and having a depth sufficient to allow for a flat spiral multiple-winding of the resilient wire in the groove and an expansion of the spiral windings of the resilient wire therewithin; and
- wherein the other end of each of said resilient wires is coupled to a respective control wire such that rotation of said pulleys in one direction to effect bending of the bending portion causes one of said resilient wires to be further wound around a respective pulley in its respective groove and the windings of the other one of said resilient wires diametrically expanded outwardly within the respective groove within which it is situated, whereby said expansion of the windings of the other one of said resilient wires prevents an excessive slackness in the control wire to which said other one of said resilient wires is coupled while maintaining at least some tension in that control wire.

10. The combination of claim 9 wherein said elongate resilient wire comprises piano wire having a substantially circular cross-section.

* * * * *